United States Patent
Lee et al.

(10) Patent No.: US 10,067,064 B2
(45) Date of Patent: Sep. 4, 2018

(54) OPTICAL FIBER CONTAINING GRAPHENE OXIDE AND REDUCED GRAPHENE OXIDE AND A GAS SENSOR CONTAINING THE SAME

(71) Applicant: RESEARCH & BUSINESS FOUNDATION SUNGKYUNKWAN UNIVERSITY, Suwon-si (KR)

(72) Inventors: Hyoyoung Lee, Suwon-si (KR); Surajit Some, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 903 days.

(21) Appl. No.: 14/160,880

(22) Filed: Jan. 22, 2014

(65) Prior Publication Data

US 2014/0204384 A1    Jul. 24, 2014

(30) Foreign Application Priority Data

Jan. 22, 2013  (KR) ......................... 10-2013-0007072

(51) Int. Cl.
*G01N 21/77* (2006.01)
*G02B 6/02* (2006.01)
*G01N 21/66* (2006.01)

(52) U.S. Cl.
CPC .  *G01N 21/7703* (2013.01); *G01N 2021/7713* (2013.01); *G01N 2021/7776* (2013.01); *Y10T 29/49885* (2015.01)

(58) Field of Classification Search
CPC ....... G01N 21/7703; G01N 2021/7776; G01N 2021/7713; Y10T 29/49885
USPC .......... 385/123–128; 356/437; 427/437, 532, 427/163.2; 29/458
See application file for complete search history.

(56) References Cited

U.S. PATENT DOCUMENTS

| | | | | |
|---|---|---|---|---|
| 8,554,022 B1* | 10/2013 | Hochberg | ......... | H01L 29/66977 257/21 |
| 8,715,532 B2* | 5/2014 | Shin | ...................... | B82Y 30/00 252/500 |
| 8,901,620 B2* | 12/2014 | Lee | ........................ | B82Y 15/00 257/12 |
| 8,940,145 B1* | 1/2015 | Chen | ...................... | C25D 13/02 204/490 |
| 9,099,376 B1* | 8/2015 | Yung | .................. | H01L 29/1606 |
| 9,105,696 B1* | 8/2015 | Dow | ................ | H01L 21/02057 |
| 9,147,881 B2* | 9/2015 | Lee | ........................ | B82Y 30/00 |
| 9,184,553 B2* | 11/2015 | Ozyilmaz | .......... | H01S 3/06791 |
| 9,233,845 B2* | 1/2016 | Gerasimos | ............ | B82Y 10/00 |

(Continued)

OTHER PUBLICATIONS

Song Y.W., et al Single-walled Carbon nanotubes for high-energy optical pulse formation, Applied Physics Letters 92, Jan. 16, 2008, p. 3.*

(Continued)

*Primary Examiner* — Akm Enayet Ullah
(74) *Attorney, Agent, or Firm* — NSIP Law

(57) ABSTRACT

An optical fiber includes a graphene oxide and a reduced graphene oxide and a gas sensor includes the optical fiber. A method for manufacturing the optical fiber includes coating a graphene oxide layer and reducing a part of the graphene oxide layer, and a method for manufacturing the gas sensor includes coating a graphene oxide layer and reducing a part of the graphene oxide layer.

10 Claims, 10 Drawing Sheets

(56) References Cited

U.S. PATENT DOCUMENTS

| | | | |
|---|---|---|---|
| 9,401,489 B2* | 7/2016 | Rafailovich | H01L 51/441 |
| 9,921,095 B2* | 3/2018 | Tichborne | G01F 23/266 |
| 2011/0010442 A1* | 1/2011 | Bimson et al. | 709/223 |
| 2011/0102068 A1* | 5/2011 | Bouchiat et al. | 327/527 |
| 2011/0285999 A1* | 11/2011 | Kim | G01N 21/552 |
| | | | 356/445 |
| 2012/0039344 A1* | 2/2012 | Kian | H01S 3/1118 |
| | | | 372/6 |
| 2012/0288227 A1* | 11/2012 | Kim | G01N 21/7703 |
| | | | 385/12 |
| 2013/0200302 A1* | 8/2013 | Miller | 252/182.32 |
| 2013/0272950 A1* | 10/2013 | Yun et al. | 423/447.1 |
| 2014/0061546 A1* | 3/2014 | Lim et al. | 252/500 |
| 2014/0127488 A1* | 5/2014 | Zhamu | C01B 31/04 |
| | | | 428/216 |
| 2014/0147648 A1* | 5/2014 | Zhamu et al. | 428/220 |
| 2014/0154941 A1* | 6/2014 | Zhamu et al. | 442/136 |
| 2014/0225569 A1* | 8/2014 | Yamazaki et al. | 320/134 |
| 2014/0308449 A1* | 10/2014 | Zhamu et al. | 427/372.2 |

OTHER PUBLICATIONS

"Self—Assembled Graphene Membrane as an Ultrafast Mode—Locker in an Erbium Fiber Laser" Published by IEEE photonics Technolgy Letters, vol. 23, issue; Dec. 1, 2011), pp. 1790-1792.*

"Graphene Oxide vs Reduced Graphene Oxide as saturable absorbers for Er-doped passively mode- locked fiber laser" by Optics Express, vol. 20, Issue 17, pp. 19463-19473, dated 2012.*

\* cited by examiner

OPTICAL FIBER CONTAINING GRAPHENE OXIDE AND REDUCED GRAPHENE OXIDE AND A GAS SENSOR CONTAINING THE SAME

CROSS-REFERENCE TO RELATED APPLICATION

This application claims the benefit of Korean Patent Application No. 10-2013-0007072 filed on Jan. 22, 2013, in the Korean Intellectual Property Office, the entire disclosure of which is incorporated herein by reference for all purposes.

BACKGROUND

1. Field

The following description relates to an optical fiber containing a graphene oxide and a reduced graphene oxide, a gas sensor including the optical fiber, a method for manufacturing the optical fiber, and a method for manufacturing the gas sensor including the optical fiber.

2. Description of Related Art

Since an optical fiber has advantages in that it is less interfered by external environments and has low information loss rate, it has been widely used in various fields for common communication networks, cable broadcasting and transmission or detection of information of various automatic devices, and the application fields of the optical fiber gas sensor have been recently diversified. A sensor using an optical fiber accomplishes its detecting performance by using elasticity by a temperature or a pressure, a phase difference of light, the Doppler effect, or others. For example, being utilized for various purposes of temperature sensors, pressure sensors, gyroscopes, speedometers, wind vanes, gas leakage sensors, etc.

Among those sensors, sensors useful for detection of gases, compounds, bio-molecules and so on have been long spotlighted, and many research results thereof have been published. Especially, a gas sensor has been used in a wide range of fields such as chemistry, pharmaceuticals, environments, medicine, etc., and it is expected that there will be more researches on gas sensors in the future. In addition, as social demands for environment preservation, safety management, etc., are increasing, the performance and the specifications required for the gas sensor are also being highly advanced.

However, in general, the gas sensor is problematic in that its selectivity to a specific gas is low, and its sensitivity is deteriorated in high humidity and strong acid or base environments. Thus, many researches are concerned with trying to overcome such problems and develop gas sensors having superior selectivity. Typically, the effect of suppression of humidity is accomplished at a high temperature of 165° C. [Cantalini, C. et al. Sensitivity to $NO_2$ and cross-sensitivity analysis to $NH_3$, ethanol and humidity of carbon nanotubes thin film prepared by PECVD. *Sens. Actuators, B* 95, 195-202 (2003)].

Accordingly, achieving high sensitivity and selectivity under high humidity conditions and maintaining high sensitivity are most difficult in realizing an effective gas sensor. It would be difficult to enable a gas sensor to have selectivity for detecting existence of a particular gas of a media containing two or more different gases under normal atmospheric conditions. This detectability is possible by virtue of different adsorption properties and reactivity properties of analytes with respect to substance. One (1)-dimensional semiconducting metal oxide nanowires have been widely researched for detection of highly sensitive gases due to their high sensitivity to different types of gases. Recent researches have reported that bonding between nano-crystals/nano-particles within a graphene-based gas sensor can improve sensor performance in view of sensitivity/detection limit, response time, or recovery time. In addition, other groups have verified that a reduced graphene oxide (rGO) can function as a gas/vapor sensor resulting in favorable outcomes.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, an optical fiber includes a core layer; and a cladding layer surrounding the core layer, wherein a graphene oxide layer and a reduced graphene oxide layer are formed in the core layer.

The graphene oxide layer and the reduced graphene oxide layer may be connected to each other and formed on a cross section of the core layer.

The core of the optical fiber may include one or more materials selected from the group consisting of glass, plastic and polymer.

The optical fiber may include a single-mode or a multi-mode optical fiber.

A gas sensor may include the optical fiber.

The gas sensor may include a light source; and a photo-detector, wherein the optical fiber is positioned between the light source and the photo-detector; and the graphene oxide layer and the reduced graphene oxide layer are connected to each other and formed on a cross section of the core layer of the optical fiber as a sensing part.

The optical fiber may include a coupler.

The gas sensor may be capable of detecting a target substance in a gas or particle state.

A target substance may be detected by using a variation in a refractive index of surfaces of the graphene oxide layer and the reduced graphene oxide layer, which are formed by being connected to each other and included in the sensing part of the gas sensor, due to an adsorption of a gas or particle.

The gas sensor may maintain a high sensitivity under a strong acid environment having a pH of about 2 or less and a base environment having a pH of about 10 or more.

The gas sensor may maintain a high sensitivity under a high humidity environment with a relative humidity of about 50% or more.

In another general aspect, a method for manufacturing an optical fiber includes coating a graphene oxide layer on a cross section of an optical fiber core layer; and reducing a part of the graphene oxide layer to form a reduced graphene oxide layer.

The method may include enabling the graphene oxide layer and the reduced graphene oxide layer to be connected to each other and to be formed on a cross-section of the optical fiber core layer.

The core of the optical fiber may include one or more materials selected from the group consisting of glass, plastic, and polymer.

The optical fiber may include a single-mode or a multi-mode optical fiber.

The reducing a part of the graphene oxide layer may be performed by photo-irradiation.

In another general aspect, a method for manufacturing a gas sensor includes coating a graphene oxide layer on a cross section of an optical fiber core layer; reducing a part of the graphene oxide layer to form a sensing part; and positioning the optical fiber formed with the sensing part between the light source and the photo-detector.

The method may include enabling the graphene oxide layer and the reduced graphene oxide layer to be connected to each other in order to form the sensing part.

The optical fiber may further include a coupler.

Figure 1:
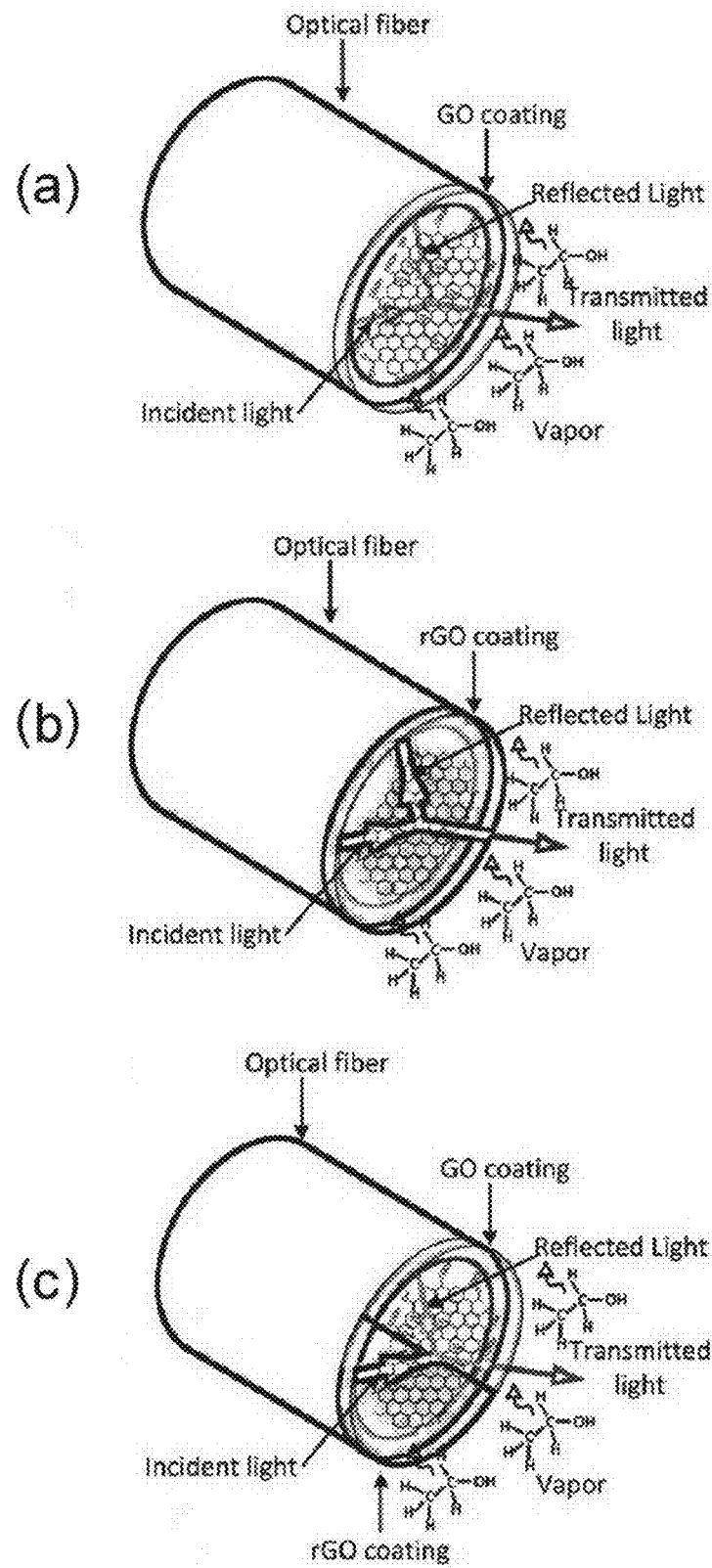
FIG. 1a is a diagram illustrating an example of an optical fiber coated with a graphene oxide (GO) layer.
FIG. 1b is a diagram illustrating an example of an optical fiber coated with a reduced graphene oxide (rGO) layer.
FIG. 1c is a diagram illustrating an example of an optical fiber, in which a graphene oxide (GO) layer and a reduced graphene oxide (rGO) layer are connected to each other and formed on a cross section of a core layer.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Throughout the following description, the term "graphene" means that multiple carbon atoms are bonded to one another through covalent bond, thereby forming polycyclic aromatic molecules, and the carbon atoms bonded through the covalent bond form a six (6) circular ring as a basic repeat unit, but may further include five (5) and/or seven (7) circular rings. Accordingly, a sheet formed of graphene appears to be a monolayer of the covalently bonded carbon atoms, but may not be limited thereto. The sheet formed of the graphene may have various structures, and the structures may vary depending on a content of the 5 and/or 7 circular rings that may be contained in the graphene. In addition, where the sheet formed of the graphene is a monolayer, the monolayer may be stacked thereby forming multiple layers, and a side surface end part of the graphene sheet may be saturated with hydrogen atoms, but may not be limited thereto.

Throughout the following description, the terms "graphene oxide" may be abbreviated as "GO." The graphene oxide may include a structure, in which a functional group containing oxygen such as a carboxyl group, a hydroxyl group or an epoxy group is bonded on monolayer graphene.

Throughout the following description, the terms "reduced graphene oxide" mean a graphene oxide, which undergoes a reduction process so that an oxygen rate is reduced, and may be abbreviated as "rGO," without being limited thereto.

Throughout the following description, the expression "a graphene oxide (GO) layer and a reduced graphene oxide (rGO) layer being connected to each other are formed" means that a GO layer and a rGO layer are arranged in the state of being connected and bonded to each other on a identical cross section of a core layer of an end of optical fiber, and may be expressed as "in the GO/rGO arrangement" or "coated with GO/rGO," without being limited thereto.

Throughout the following description, the term "VOC" stands for a volatile organic compound and may be used in plural like VOCs. For example, VOCs may include ethanol, nitromethane, acetone, methanol, tetrahydrofuran (THF), diethylamine, hydrazine, dichloromethane (MC), or combinations thereof, but may not be limited thereto.

Throughout the following description, the term "POF" stands for polymeric optical fiber, and a core layer and/or a cladding layer may contain at least one polymer material, without being limited thereto.

In one general aspect, an optical fiber includes a core layer and a cladding layer surrounding the core layer, in which a graphene oxide (GO) layer and a reduced graphene oxide (rGO) layer are connected to each other and formed on a cross section of the core layer.

The core of the optical fiber may include one or more selected from the group consisting of glass, plastic and polymer, but may not be limited thereto.

The optical fiber may include a single-mode or multi-mode optical fiber, but may not be limited thereto.

In another general aspect, a gas sensor includes the above-described optical fiber.

The gas sensor may include a light source; a photodetector; and the optical fiber positioned between the light source and the light detector, wherein a graphene oxide layer and a reduced graphene oxide layer being connected to each other are formed on a cross section of the core layer of the optical fiber, as a sensing part, without being limited thereto.

The light source may include a light source of an entire range of ultraviolet ray (UV), visible ray (VIS) or infrared ray (IR), but may not be limited thereto.

The optical fiber may further include a coupler, but may not be limited thereto. For example, the coupler may be a Y-coupler or a T-coupler, but may not be limited thereto.

The sensing part may be formed in the manner that a graphene oxide layer and a reduced graphene oxide layer, which are obtained by coating a graphene oxide layer on a cross section of an end of optical fiber and reducing a part of the coating layer being connected to each other are formed on the cross section of the end of the optical fiber.

The gas sensor may be capable of detecting a target substance in a gas or particle state, but may not be limited thereto.

The target substance may be detected by using a variation in a refractive index of surfaces of the graphene oxide layer and the reduced graphene oxide layer, which are connected to each other and included in the sensing part of the gas sensor, due to an adsorption of a gas or particle, but may not be limited thereto. In the gas sensor, since the refractive index of the surfaces of the graphene oxide layer and the reduced graphene oxide layer, which are connected to each other in the sensing part of the optical fiber gas sensor, is sensitively responsive depending on adsorption of a gas, particle and so on, the gas sensor can be widely applied to various fields such as semiconductors and environmental technologies for the purposes of uses for a gas and particle (aerosol, nano-particle, etc.) control sensor, monitoring of environmental pollution, chemical component analysis, NO monitoring and others. For example, the gas sensor may sense a gas or particles of a compound selected from the group consisting of $H_2$, CO, $CO_2$, $O_2$, $NO_x$, $CO_2$, dimethyl methylphosphate (DMMP), $CH_4$, $NH_3$ $CH_3OH$, liquefied petroleum gas (LPG), $H_2S$, benzene, $CH_3SH$, toluene, VOC and combinations thereof, but may not be limited thereto.

The gas sensor can selectively sense VOC gases. Since the gas sensor includes the sensing part, in which the hydrophilic graphene oxide layer and the hydrophobic reduced graphene oxide layer are connected to each other and formed on a cross section of the core layer of the optical fiber, it can selectively sense various VOC gases absorbed on the surface of the sensing part consisting of the two graphene oxide layers having different properties. The gas sensor can discriminate tetrahydrofuran and dichloromethane, which are hardly discriminated in the field of the gas sensor.

The gas sensor can maintain a high sensitivity under a strong acid (pH of approximately 2 or less) and a base (pH of approximately 10 or more) environment, but may not be limited thereto.

The gas sensor can maintain a high sensitivity under a high humidity (a relative humidity of approximately 50% or more) environment, but may not be limited thereto.

Since the gas sensor includes the graphene oxide layer containing various oxygen functional groups, it can provide rapid response and maintain a high sensitivity even under a high humidity and strong acid or base environment.

In another general aspect, a method for manufacturing the above-described optical fiber includes coating a graphene oxide layer on a cross section of a core layer of the optical fiber; and reducing a part of the graphene oxide layer to form a reduced graphene oxide layer, whereby the graphene oxide layer and the reduced graphene oxide layer being connected to each other are formed on a cross section of the core layer of the optical fiber.

FIG. 1 is a diagram illustrating an example of an optical fiber. FIG. 1a illustrates an example of an optical fiber, in which a cross section of an end of the optical fiber is coated only with a graphene oxide (GO) layer, FIG. 1b illustrates an example of an optical fiber coated only with a reduced graphene oxide (rGO) layer, and FIG. 1c illustrates an example of an optical fiber, in which a graphene oxide (GO) layer and a reduced graphene oxide (rGO) layer are connected to each other and formed on a cross section of a core layer of the optical fiber.

In an example, cutting the end of the optical fiber in the longitudinal direction and trimming the cross section to be plane may be performed prior to the above-described coating process, but the present disclosure may not be limited thereto. A graphene oxide (GO) solution may be dropped on the cross section of the optical fiber, which has underwent the trimming process, and dried so that a graphene oxide (GO) layer can be formed or coated on the cross section of the optical fiber as shown in FIG. 1a, but the present disclosure may not be limited thereto.

The core of the optical fiber may include one or more materials selected from the group consisting of glass, plastic and polymer, but may not be limited thereto. The optical fiber may include a single-mode or a multi-mode optical fiber, but may not be limited thereto.

For example, reducing a part of the graphene oxide layer may be performed by photo-irradiation, but may not be limited thereto. Upon the photo-irradiation, a wavelength may include light in a range of from approximately 1 nm to approximately $10^6$ nm, but may not be limited thereto.

In The time for the photo-irradiation may be approximately 3,000 seconds or less, e.g., from approximately one second to approximately 3,000 seconds, but may not be limited thereto.

Figure 2:
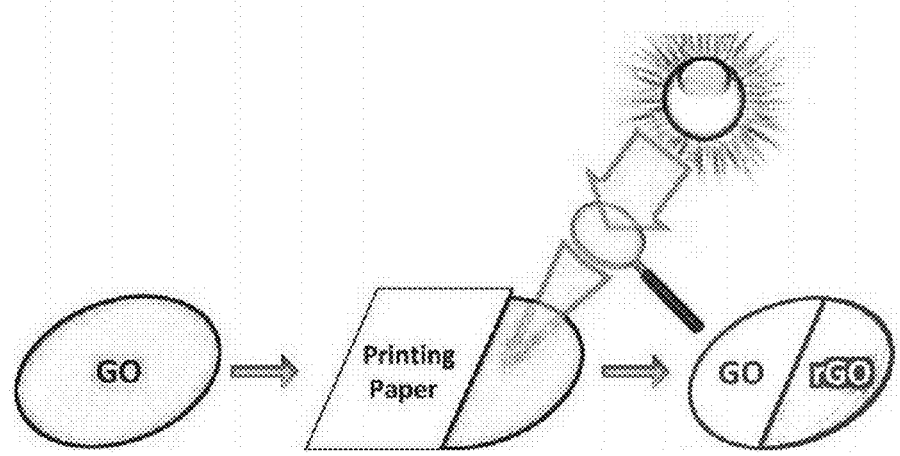
FIG. 2 is a diagram illustrating an example of a process for forming an rGO layer.

FIG. 2 illustrates an example of a process for forming the reduced graphene oxide (rGO) layer. For example, optical fiber with a cross section thereof being coated with the graphene oxide (GO) layer is fixed, and as shown in FIG. 2, half of the section coated with the graphene oxide (GO) layer is covered with a printing paper. Thereafter, once photo-irradiation, e.g., irradiation of visible light or solar ray is performed by using a convergent lens to the part that is not covered with the printing paper, the graphene oxide (GO) layer can be reduced to the reduced graphene oxide (rGO) layer, and the optical fiber in the GO/rGO arrangement, which includes both the half graphene oxide (GO) layer and the half reduced graphene oxide (rGO) layer as shown in FIG. 1c, can be obtained, without being limited thereto.

There is provided a method for manufacturing a gas sensor including the above-described optical fiber, which includes: coating a graphene oxide layer on a cross section of an optical fiber core layer; reducing a part of the graphene oxide layer to enable the graphene oxide layer and the reduced graphene oxide layer to be connected to each other and thus to form a sensing part; and positioning the optical fiber formed with the sensing part between a light source and a photo-detector.

The optical fiber gas sensor of this example can be completed by manufacturing an optical fiber including a sensing part, in which a graphene oxide layer and a reduced graphene oxide layer being connected to each other are formed on a cross section of the optical fiber core layer through a method of coating a graphene oxide layer on a cross section of the optical fiber core layer and reducing a part of the graphene oxide layer.

The optical fiber may further include a coupler, but may not be limited thereto. For example, the coupler may be a Y-coupler or a T-coupler, but may not be limited thereto.

Hereinafter, examples and drawings will be described, but the present disclosure may not be limited to the examples and the drawings.

Preparation Example: Preparation of the Graphene Oxide

A graphene oxide was prepared by processing natural graphite powders by using sulfuric acid, potassium permanganate, and sodium nitrate and performing the methods of Hummers and Offenman.

Example 1: Manufacture of the Polymer Optical Fiber Coated with the GO Layer

Polymer optical fiber (POF) was cut by using a sharp knife, and a cross section thereof was trimmed to be uniform and plane. A 3 μL 1 mg/mL graphene oxide (GO) solution was dropped on the trimmed cross section of the POF, and the POF, on which the GO was dropped, was continuously dried at 60° C. to form a GO coating layer on the cross section so that the POF coated with the GO layer was manufactured, as shown in FIG. 1a.

Example 2: Manufacture of the Polymer Optical Fiber in the GO/rGO Arrangement

The POF coated with the GO layer, which was manufactured in Example 1, was fixed, and half of the coated cross section was covered by using a printing paper. Thereafter, solar ray was intensively irradiated to the other half of the GO coating layer that was not covered by the printing paper. By removing the printing paper, the POF had a structure of the GO/rGO arrangement, in which the half GO layer and the half rGO layer are connected to each other, and can be used as a sensing part, as shown in FIG. 1c.

Example 3: Manufacture of the Polymer Optical Fiber Coated with the rGO Layer

For a controlled experiment, solar ray was irradiated to the cross section of the POF coated with the GO layer, which was manufactured in Example 1, by using a convergent lens without the printing paper, so that the POF coated with the rGO layer was obtained as shown in FIG. 1b.

Figure 3:
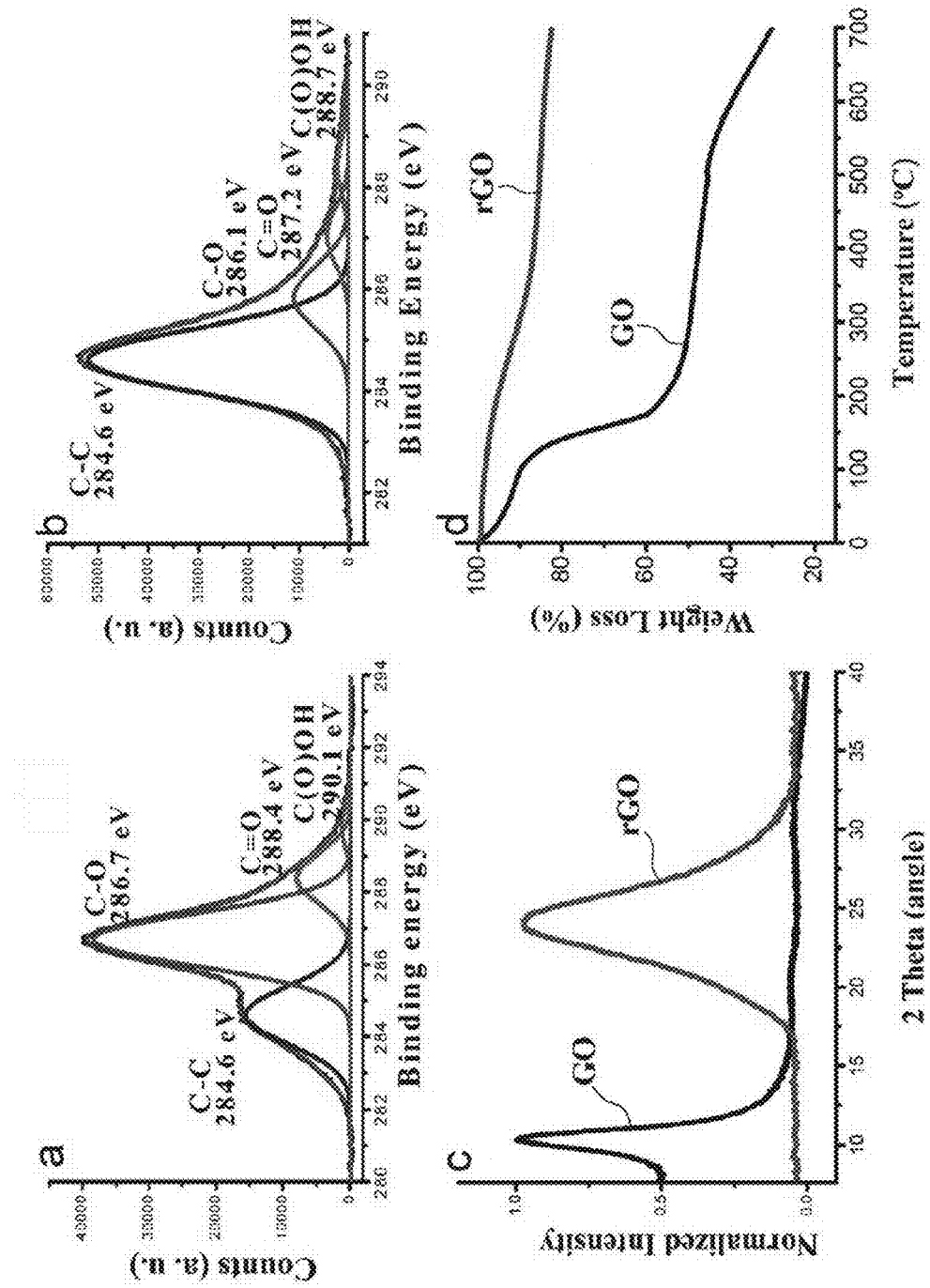
FIG. 3a is a diagram illustrating an example of an XPS spectrum of C 1s of a GO layer, which was measured by high-resolution X-ray photoemission spectroscopy (XPS).
FIG. 3b is a diagram illustrating an example of an XPS spectrum of C 1s of a rGO layer.
FIG. 3c is a diagram illustrating an example of an XRD spectrum showing crystalline structures of a GO layer and a rGO layer.
FIG. 3d is a diagram illustrating an example of a thermogravimetric analysis results for a GO layer and a rGO layer.

Example 4: Analysis of Characteristics of the Polymer Optical Fiber Coated with the GO Layer, the rGO Layer and the GO/rGO Layer A characteristic analysis experiment for the POF obtained in Examples 1 to 3 was conducted. All X-ray photoemission spectroscopy (XPS) measurements were implemented at 100 W by SIGMA PROBE (ThermoVG, Britain) using a solid color Al—Kα X-ray source. An XRD pattern was obtained by using D8 Advance instrument (Germany) using Cu—Kα radiation. The thermal characteristic of the rGO was measured by thermogravimetric analysis (TGA; Institute for Polymer Research, TGA 1000 Plus), and FIG. 3 shows the analysis results.

FIG. 3a illustrates an example of an XPS spectrum of C 1s of the graphene oxide (GO) layer, which was measured by high-resolution X-ray photoemission spectroscopy (XPS), FIG. 3b illustrates an example of an XPS spectrum of C 1s of the reduced graphene oxide (rGO) layer, FIG. 3c illustrates an example of an XRD spectrum showing crystalline structures of the graphene oxide (GO) layer and the reduced graphene oxide (rGO) layer, and FIG. 3d illustrates an example of a graph showing thermogravimetric analysis results of the graphene oxide (GO) layer and the reduced graphene oxide (rGO) layer.

As shown in FIG. 3a, the GO layer manufactured in this example exhibited a significantly high oxygen atom ratio (C/O=2.2). To the contrary, as shown in FIG. 3b, the C/O ratio of the rGO layer was 11.6. From the XPS data, it was confirmed that the rGO layer was reduced to have high quality, and it was concluded that the rGO layer contains substantially less oxygen, compared to the GO layer. Also, through the XRD spectrums of the GO layer and the rGO layer, it was confirmed that the GO layer was reduced to the rGO layer as shown in FIG. 3c. The TGA was used for evaluating the quality of the rGO layer, compared to the GO layer. FIG. 3d shows TGA plots of the GO layer and the rGO layer. As shown in FIG. 3d, the weight of the GO layer was mostly lost between 100° C. and 200° C. This shows that CO and $CO_2$ were discharged from the most unstable functional group during thermal decomposition. The whole weight loss of the GO layer in this example was 72% at the temperature of less than 700° C. Meanwhile, the whole weight loss of the rGO layer was 18.6%.

Example 5: Manufacture of the POF Gas Sensor in the GO/rGO Arrangement

Figure 4:
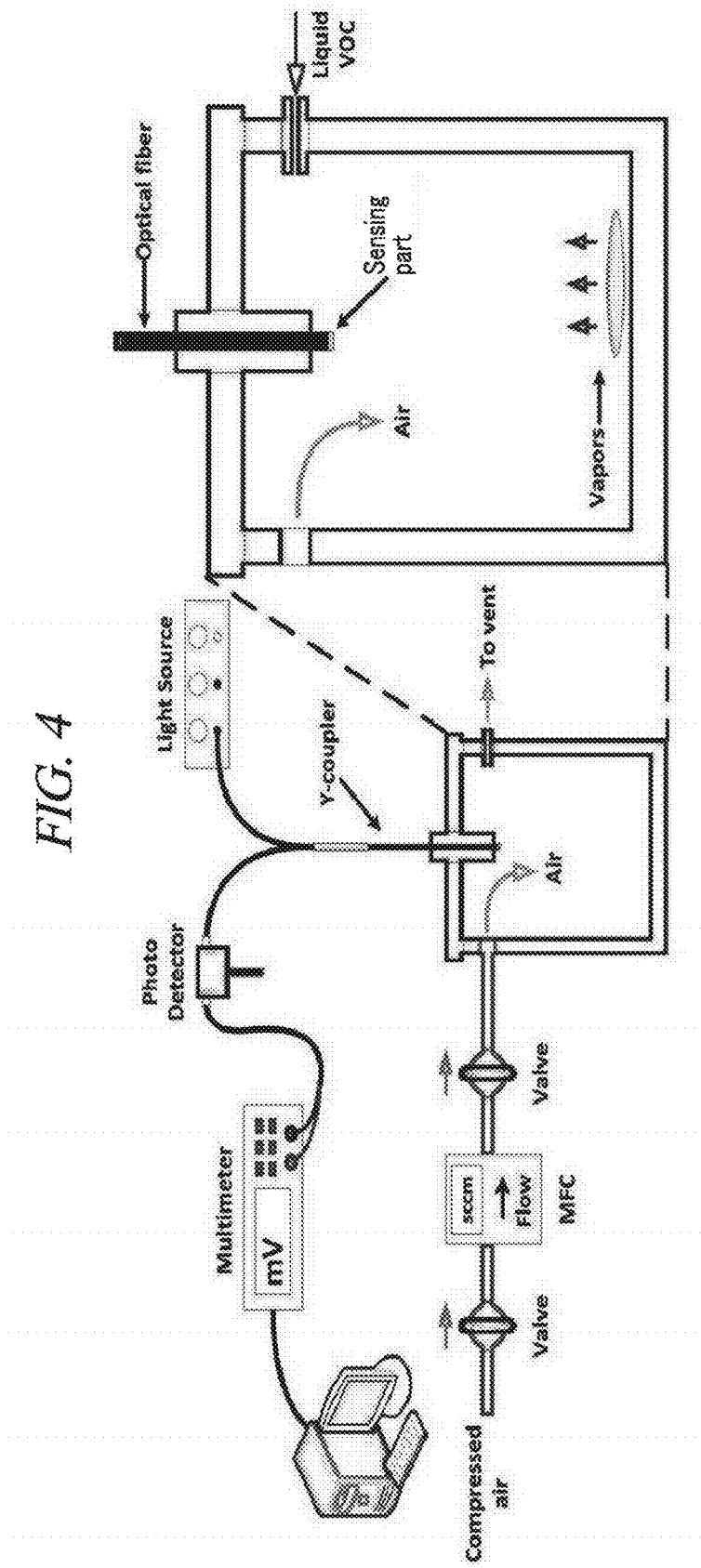
FIG. 4 is a diagram illustrating an example of an experimental apparatus for detection of various VOCs by optical fiber.

FIG. 4 is a schematic view illustrating an example of an experimental apparatus for detection of various VOCs by the optical fiber.

For reflection signal detection, a 1×2 optical fiber coupler (50:50, Industrial Fiber Optics Inc., IF-562), which can connect the POF manufactured in Examples 1 to 3, the light source, and the photo-detector interface to one another, was used. The POF manufactured in Examples 1 to 3 was placed between the light source and the photo-detector by using a Y-coupler such that the gas sensor was completed as illustrated in FIG. 4.

Figure 5:
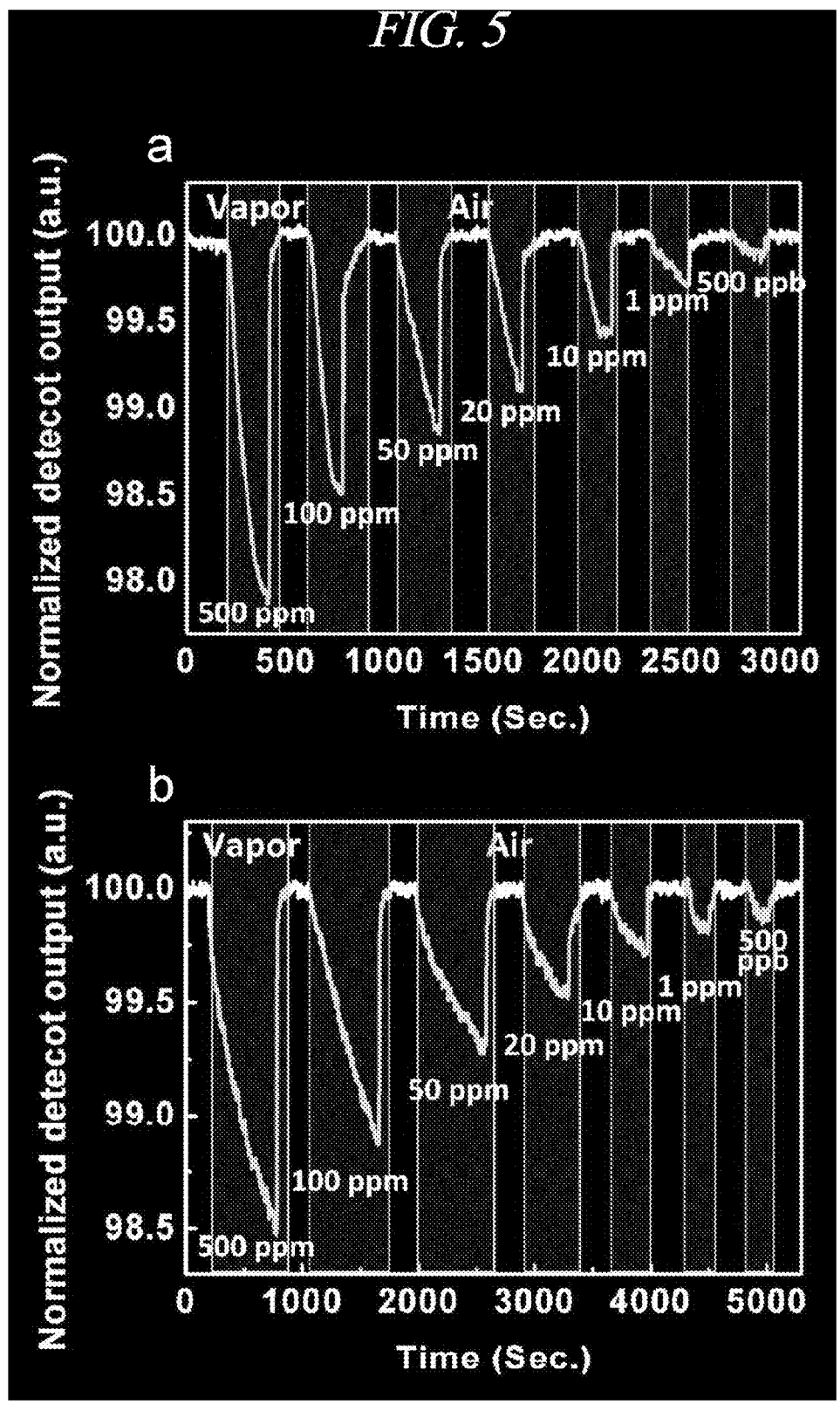
FIG. 5a is a diagram illustrating an example of an adsorption and desorption reaction of a polymer optical fiber (POF) gas sensor coated with a GO layer to acetone vapor (500 ppb to 500 ppm).
FIG. 5b is a diagram illustrating an example of an adsorption and desorption reaction of a POF gas sensor coated with a rGO layer to acetone vapor (500 ppb to 500 ppm).
Figure 6:
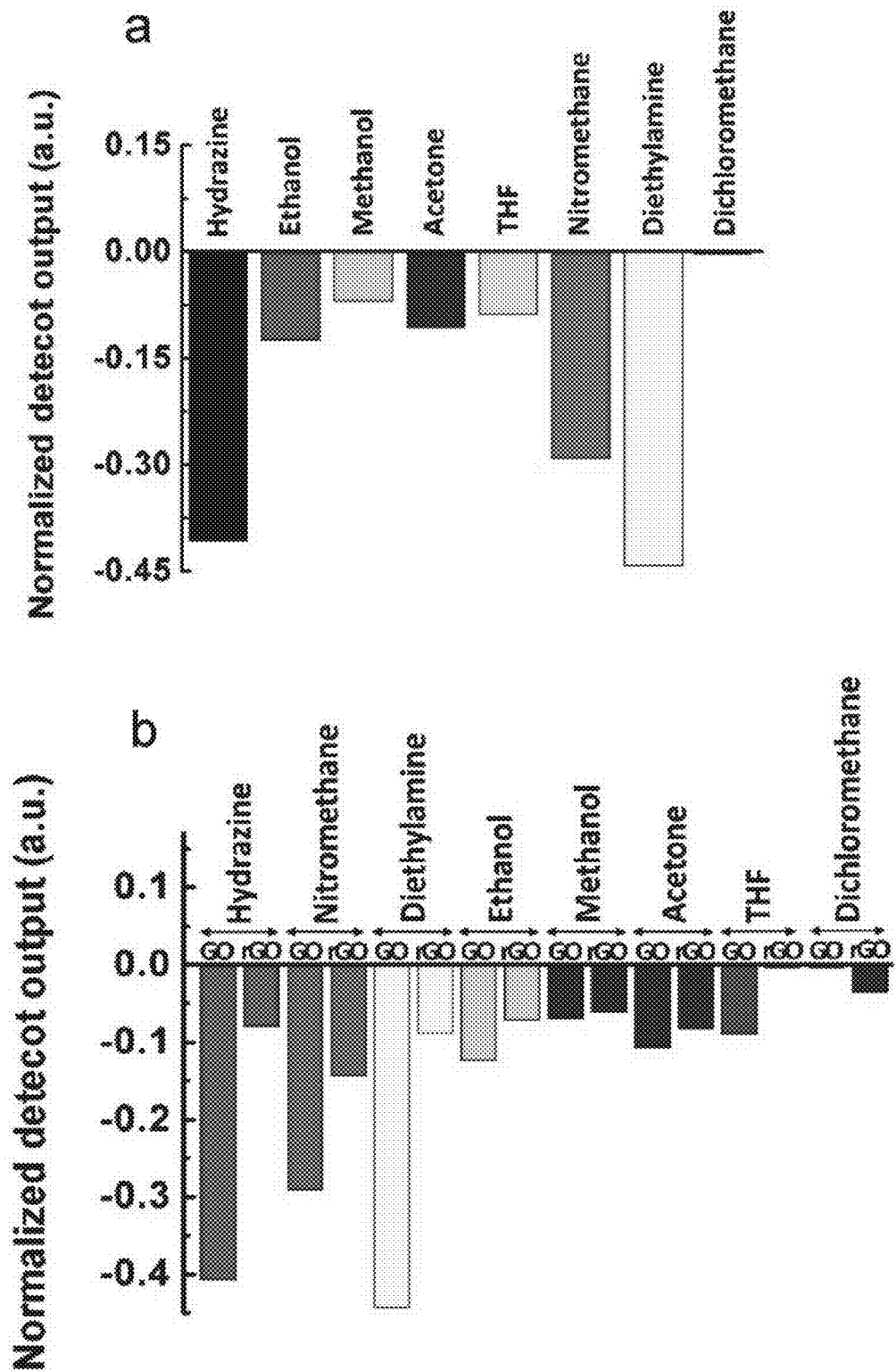
FIG. 6a is a diagram illustrating an example of a sensing response of a POF gas sensor coated with a GO layer to various VOCs.
FIG. 6b is a diagram illustrating an example of a sensing response of each of a POF gas sensor coated with a GO layer and a POF gas sensor coated with a rGO layer to various VOCs.

Experimental Example 1: VOC Detection Using the POF Gas Sensor Coated with the GO Layer and the rGO Layer As shown in FIG. 4, each of the coated cross sections of the POF coated with the GO layer and the POF coated with the rGO layer was placed in an experiment chamber, and a pre-informed amount of VOC was injected thereinto in order to obtain various VOC concentrations. For the VOC, hydrazine, ethanol, methanol, dichloromethane, acetone, tetrahydrofuran, nitromethane, diethylamine and so on were used. The sensor performance was tested by using a blue light source (a spectrum range of from 450 nm to 495 nm, and an optical power of 2 mW). Reflected light intensity was measured by using an optical diode detector (PDA36A, Thorlab) having a spectrum range of from 350 nm to 1,100 nm and being connected to a computer interface digital multimeter (2700, Keithley). In order to facilitate signal recovery, UV irradiation (254 nm, VL-4.LC) was used depending on necessity during the experiments. All the experiments were conducted in a dark room. FIGS. 5 and 6 illustrate example of the experiment results.

FIG. 5a illustrates an example of a graph showing adsorption and desorption reaction of the polymer optical fiber (POF) gas sensor coated only with the graphene oxide layer to acetone vapor (from 500 ppb to 500 ppm), and FIG. 5b illustrates an example of a graph showing adsorption and desorption reaction of the POF gas sensor coated only with the reduced graphene oxide (rGO) layer to acetone vapor (from 500 ppb to 500 ppm). As shown in the examples of FIG. 5a and FIG. 5b, while the acetone vapor was continuously injected into the gas sensor in the concentration of from 500 ppb to 500 ppm, the POF gas sensor coated with only the GO layer or the rGO layer recorded change of reflected optical power and exhibited small change in reflected optical power as a dilution ratio of the acetone vapor is large. In addition, it was observed that the POF coated only with the GO layer was recovered to the baseline in a shorter time than that for the POF coated only with rGO layer. This means that the recovery of the POF gas sensor coated only with the GO layer is better than that for the POF gas sensor coated only with the rGO layer.

FIG. 6a illustrates an example of a graph showing sensing response of the POF gas sensor coated only with the graphene oxide (GO) layer to various VOCs, and FIG. 6b illustrates an example of a graph showing sensing response of each of the POF gas sensor coated only with the graphene oxide (GO) layer and the POF gas sensor coated only with the reduced graphene oxide (rGO) layer to various VOCs. As shown in FIG. 6a and FIG. 6b, it was confirmed that the POF gas sensor coated only with the GO layer and the POF gas sensor coated only with the rGO layer exhibited different sensitivities to various vapors in the significantly low concentration of 500 ppb. The intensity of the reflected optical response of each of the POF gas sensor coated only with the GO layer and the POF gas sensor coated only with the rGO layer was the highest at the same concentration with respect to diethylamine and nitromethane vapors and the lowest with respect to methanol and dichloromethane vapors. In addition, the POF gas sensor coated only with the GO layer exhibited high sensitivity to VOCs containing a polar functional group, compared to the POF gas sensor coated only with the rGO layer.

Experimental Example 2: Measurement of the Intensity of the Reflected Optical Response Using the POF Gas Sensor Containing GO FIG. 7 illustrates an example of a schematic view showing an optical fiber connected to a coupler thereby having two tips.

Figure 7:
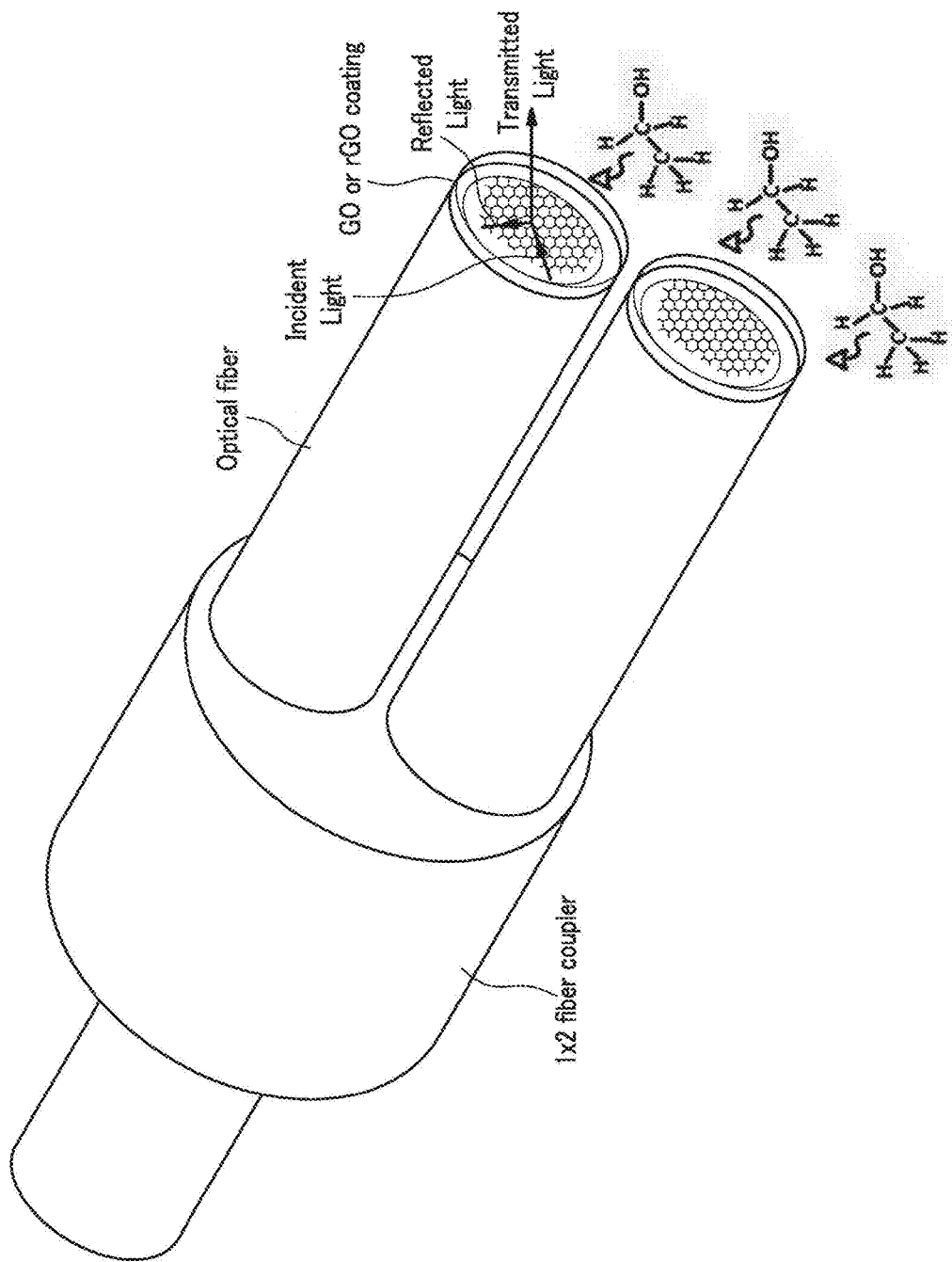
FIG. 7 is a diagram illustrating an example of an optical fiber connected to a coupler thereby having two tips.

In order to identify selectivity of the POF gas sensor coated with the GO layer and the rGO layer with respect to VOCs, as shown in FIG. 7, the intensity of the reflected optical response was measured by using the POF having two tips. At this time, for the POF having two tips, the POF, in which a coating layer of the tips is GO-rGO, rGO-rGO or GO-GO, was used, and FIG. 8a shows an example of the experiment results.

Figure 8:
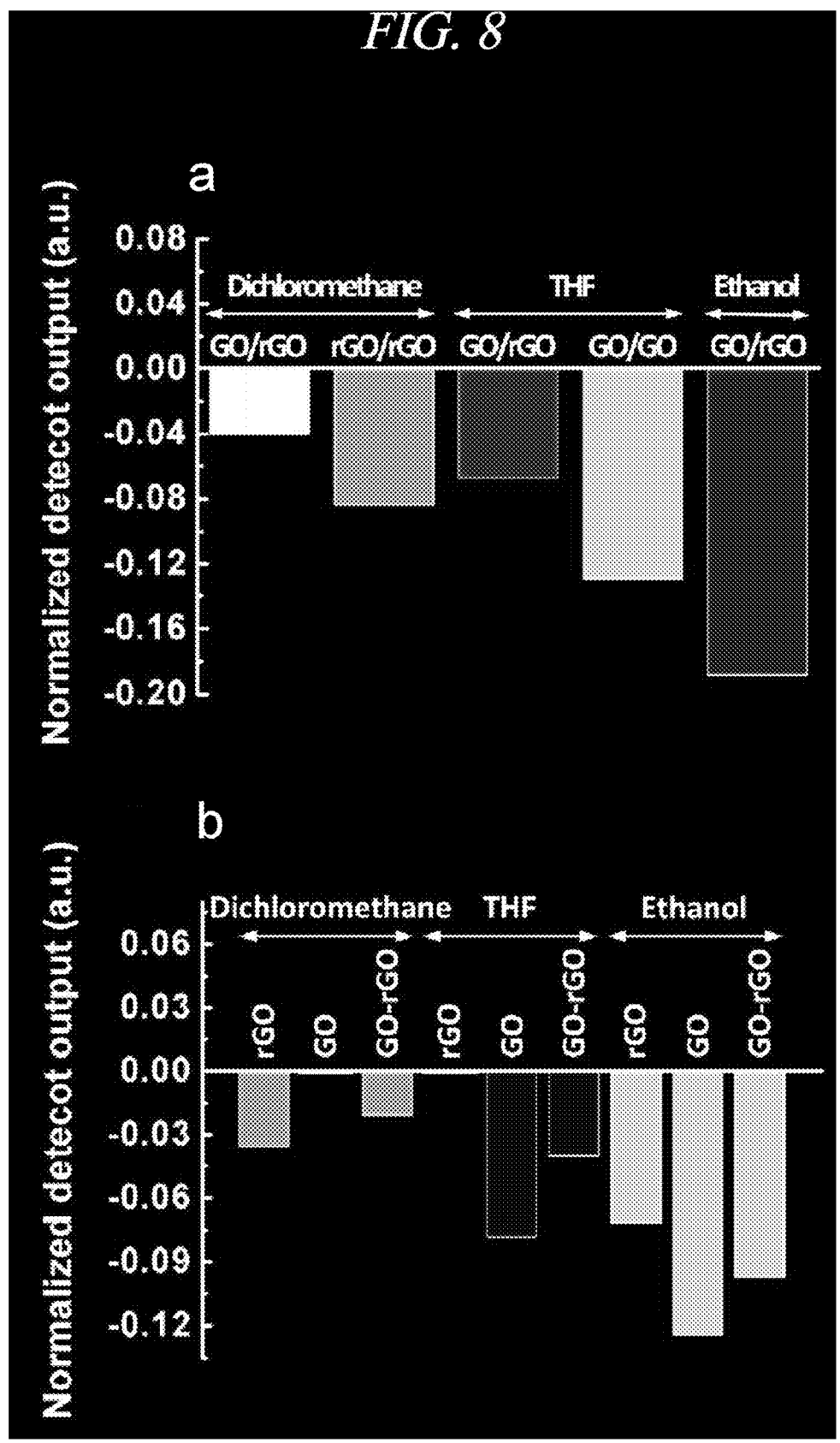
FIG. 8a is a diagram illustrating an example of a sensing response of a POF gas sensor having two tips to VOCs, in which each of the tips contains a GO-rGO layer, an rGO-rGO layer and a GO-GO layer.
FIG. 8b is a diagram illustrating an example of a sensing response, to VOCs, of a POF gas sensor coated with a GO layer and a POF gas sensor coated with a rGO sensor layer, and a POF gas sensor, in which a GO layer and a rGO layer being connected to each other are formed on a cross section of a core layer.

FIG. 8a illustrates an example of a graph showing sensing response of the POF gas sensors each having two tips and containing GO-rGO, rGO-rGO and GO-GO, respectively. The POF gas sensors containing GO clearly exhibited selectivity to VOCs. As shown in FIG. 8a, the POF gas sensor of GO-rGO exhibited half of the response value of the POF gas sensor containing rGO-rGO with respect to dichloromethane, and the POF gas sensor containing GO-rGO exhibited half of the response value of the POF gas sensor containing GO-GO with respect to THF. Accordingly, it was confirmed that hydrophilic GO exhibits selectivity to a gas when it is used as a gas sensor.

Experimental Example 3: Measurement of the Intensity of the Reflected Optical Response Using the POF Gas Sensor in the GO/rGO Arrangement In order to identify selectivity of the POF gas sensor, in which the GO layer and the rGO layer are connected to each other and formed on a cross section of the core layer (in the GO/rGO arrangement), to VOCs, a reflected optical measurement experiment was conducted by using the same method as used in Experimental Example 2, and FIG. 8b shows the results.

FIG. 8b illustrates an example of a graph showing sensing response of the POF gas sensor coated only with the graphene oxide (GO) layer and the POF gas sensor coated only with the reduced graphene oxide (rGO) layer, and the POF gas sensor in the GO/rGO arrangement, in which the graphene oxide (GO) layer and the reduced graphene oxide (rGO) layer are connected to each other and formed on a cross section of the core layer. As shown in FIG. 8b, the POF gas sensor in the GO/rGO arrangement exhibited half of the response value of the POF gas sensor coated only with the rGO layer with respect to dichloromethane, and the POF gas sensor in the GO/rGO arrangement exhibited half of the response value of the POF gas sensor coated only with the GO layer with respect to THF. In addition, it was observed that the reflected optical response of the POF gas sensor in the GO/rGO arrangement with respect to ethanol was lower than that of the POF gas sensor coated only with the GO layer and higher than the response of the POF gas sensor coated only with the rGO layer. These results are natural as a result of difference in sensitivity between GO and rGO with respect to ethanol. Based on the results, a mixing ratio of an unknown gas mixture can be identified by using the POF gas sensor in the GO/rGO arrangement.

Experimental Example 4: Analysis and Evaluation of a Gas Mixture by Means of the POF Gas Sensor in the GO/rGO Arrangement In order to identify a mixing ratio of a gas mixture, sensitivity response experiments were conducted by using the POF gas sensor in the GO/rGO arrangement as shown in FIG. 1c, the POF gas sensor coated only with the GO layer as shown in FIG. 1a, and the POF gas sensor coated only with the rGO layer as shown in FIG. 1b with respect to dichloromethane in a concentration 500 ppb, THF and mixtures thereof. Table 1 below shows an example of the sensitivity response results for each of the gas sensors.

TABLE 1

|  | GO | rGO | GO/rGO | Ratio of MC:THF |
|---|---|---|---|---|
| MC | 0 | −0.03728303 | −0.02086807 | — |
| THF | −0.08868249 | 0 | −0.04040823 | — |
| MC:THF (50:50) | −0.04143215 | −0.02245723 | −0.03122931 | approximately 50:50 |
| MC:THF Mixture 1 | −0.05877224 | −0.01396425 | −0.03655617 | approximately 30:70 |
| MC:THF Mixture 2 | −0.02667822 | −0.03224376 | −0.02859109 | approximately 70:30 |

As shown in Table 1, it was confirmed that sensitivity intensity of the rGO layer of the POF gas sensor in the GO/rGO arrangement with respect to MC, and the GO layer of the same POF gas sensor with respect to THF was a ratio of approximately 1:2 at the same concentration as shown in FIG. 7b, and the ratio of the intensity was maintained even in case of the presence of a 50:50 mixture of MC:THF. The total sensitivity intensity, which corresponds to the sum of the sensitivity intensity values of the POF gas sensor coated with the GO layer and the POF gas sensor coated with the rGO layer with respect to VOC gases or gas mixtures thereof, was double the sensitivity intensity of the POF gas sensor in the GO/rGO arrangement. As a result of measuring a gas mixing ratio of MC:THF Mixture 1 and MC:THF Mixture 2, of which a mixing ratio is unknown, by using the response results of the sensitivity intensity, it was confirmed that the mixing ratios of MC:THF was approximately 30:70 and approximately 70:30, respectively.

Experimental Example 5: Measurement of Sensitivity Variation Depending on pH of the POF Gas Sensor Containing GO In order to verify that GO is an essential element for the sensing ability and adsorption under an extremely strong acid or base condition, sensitivity testing was performed for ethanol, nitromethane and diethylamine vapors in GO suspensions, which have different pH values (1, 5, 7 and 11), and FIG. 9 shows an example of the results.

Figure 9:
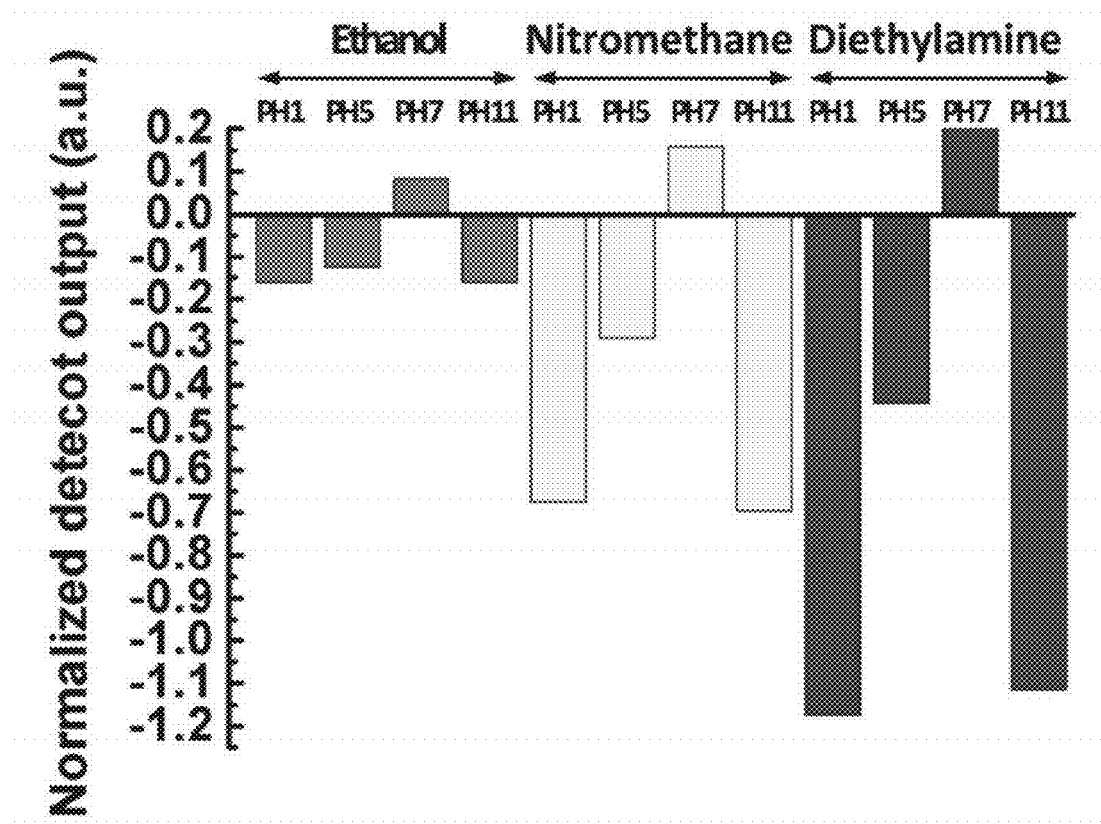
FIG. 9 is a diagram illustrating an example of a gas sensing property of a POF gas sensor at various pHs.

FIG. 9 illustrates an example of a graph showing a gas sensing property of the POF gas sensor at various pHs. At pHs 1 and 11, the GO may contain a large amount of positive or negative charges. Accordingly, as shown in FIG. 9, far high sensitivity was exhibited, compared to the result when pH was 7, and also, higher sensitivity than that in case of pH 5 was exhibited. This confirms that the POF gas sensor in the GO/rGO arrangement exhibits high sensitivity even in the strong acid or base condition.

Experimental Example 6: Measurement of Sensitivity Variation of the POF Gas Sensor Containing GO Depending on Humidity In order to verify that the POF gas sensor in the GO/rGO arrangement exhibits high sensitivity under high humidity, sensing response testing was performed under a maximum humidity condition by using the POF gas sensor coated with the GO layer and the POF gas sensor coated with the rGO layer with respect to ethanol, nitromethane, acetone, methanol, THF, diethylamine, hydrazine, and dichloromethane in a concentration of 500 ppb, and FIG. 10 shows an example of the results.

Figure 10:
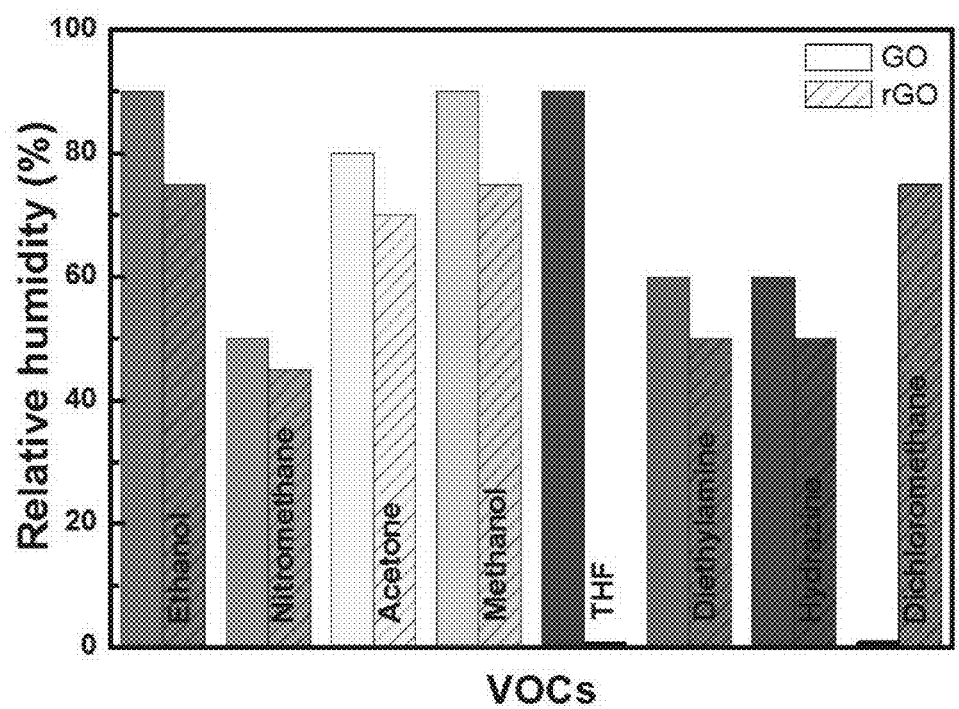
FIG. 10 is a diagram illustrating an example of sensing properties of a POF gas sensor coated with a GO layer and a POF gas sensor coated with an rGO layer with respect to VOCs in a maximum humidity environment.

FIG. 10 illustrates an example of a graph showing sensing properties of the POF gas sensor coated with the graphene oxide (GO) layer and the POF gas sensor coated only with the reduced graphene oxide (rGO) layer with respect to various VOCs under a maximum humidity environment. As shown in FIG. 10, the POF gas sensor coated with the GO layer could sense VOCs under the high humidity condition with high sensitivity, compared to the POF gas sensor coated with the rGO layer. It was confirmed that the POF gas sensor coated with the GO layer exhibits high sensitivity with respect to ethanol (relative humidity 90%), nitromethane (relative humidity 50%), acetone (relative humidity 80%), methanol (relative humidity 90%), THF (relative humidity 90%), diethylamine (relative humidity 60%) and hydrazine (relative humidity 60%).

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

We claim:

1. A gas sensor, comprising:
   a light source;
   a photo-detector, and
   an optical fiber, the optical fiber comprising:
      a core layer; and
      a cladding layer surrounding the core layer,
   wherein a graphene oxide layer and a reduced graphene oxide layer are formed in a common cross section of the core layer, and
   wherein the optical fiber is positioned between the light source and the photo-detector; and the graphene oxide layer and the reduced graphene oxide layer are connected to each other and formed on a cross section of the core layer of the optical fiber as a sensing part.

2. The optical fiber of claim 1, wherein the core of the optical fiber comprises one or more materials selected from the group consisting of glass, plastic and polymer.

3. The optical fiber of claim 1, wherein the optical fiber comprises a single-mode or a multi-mode optical fiber.

4. The gas sensor of claim 1, wherein the optical fiber further comprises a coupler.

5. The gas sensor of claim 1, wherein the gas sensor is capable of detecting a target substance in a gas or particle state.

6. The gas sensor of claim 1, wherein a target substance is detected by using a variation in a refractive index of surfaces of the graphene oxide layer and the reduced graphene oxide layer, which are formed by being connected to each other and included in the sensing part of the gas sensor, due to an adsorption of a gas or particle.

7. The gas sensor of claim 1, wherein the gas sensor maintains a high sensitivity under a strong acid environment having a pH of about 2 or less and a base environment having a pH of about 10 or more.

8. The gas sensor of claim 1, wherein the gas sensor maintains a high sensitivity under a high humidity environment with a relative humidity of about 50% or more.

9. The optical fiber of claim 1, wherein the graphene oxide layer and the reduced graphene oxide layer are connected to each other.

10. The optical fiber of claim 1, wherein an upper half of the common cross section comprises the graphene oxide layer and a lower half of the common cross section comprises the reduced graphene oxide layer.

\* \* \* \* \*